(12) United States Patent
Ngo

(10) Patent No.: US 8,659,436 B2
(45) Date of Patent: Feb. 25, 2014

(54) VEHICLE OPERATOR ALERTNESS MONITORING SYSTEM

(75) Inventor: Gordon John Hann Ngo, London (CA)

(73) Assignee: OES, Inc., London, Ontario (CA)

(*) Notice: Subject to any disclaimer, the term of this patent is extended or adjusted under 35 U.S.C. 154(b) by 397 days.

(21) Appl. No.: 13/022,911

(22) Filed: Feb. 8, 2011

(65) Prior Publication Data

US 2011/0193707 A1 Aug. 11, 2011

Related U.S. Application Data

(60) Provisional application No. 61/302,198, filed on Feb. 8, 2010.

(51) Int. Cl.
*G08B 23/00* (2006.01)
(52) U.S. Cl.
USPC ............................................ 340/576; 600/519

(58) Field of Classification Search
USPC .................. 340/576, 575, 439; 600/519, 509
See application file for complete search history.

(56) References Cited

U.S. PATENT DOCUMENTS

| 7,113,100 B2* | 9/2006 | Yoshinori et al. ............. 340/576 |
| 2002/0121981 A1* | 9/2002 | Munch ........................... 340/576 |
| 2003/0043045 A1* | 3/2003 | Yasushi et al. ................ 340/576 |
| 2004/0046666 A1* | 3/2004 | Yasuchi ......................... 340/576 |
| 2008/0122636 A1* | 5/2008 | Matos ........................... 340/576 |

* cited by examiner

*Primary Examiner* — Thomas Mullen
(74) *Attorney, Agent, or Firm* — Carlson, Gaskey & Olds

(57) ABSTRACT

An exemplary vehicle operator alertness monitoring system includes a heart rate monitor and a vehicle operator alert module. The vehicle operator alert module communicates with the heart rate monitor and determines whether a vehicle operator's heart rate is within an acceptable range. The vehicle operator alert module is configured to alert the vehicle operator when the vehicle operator's heart rate is outside of the acceptable range to assist the vehicle operator at maintaining alert control over the vehicle.

18 Claims, 1 Drawing Sheet

VEHICLE OPERATOR ALERTNESS MONITORING SYSTEM

CROSS REFERENCE TO RELATED APPLICATIONS

This application claims priority to U.S. Provisional Application No. 61/302,198 which was filed on Feb. 8, 2010.

BACKGROUND OF THE INVENTION

Sleep deprivation and fatigue are potential problems for vehicle operators including automobile drivers. Different approaches have been proposed for detecting driver fatigue. One proposed approach is to monitor a driver's head position to determine if the driver's head moves in a manner that corresponds to falling asleep. This method only works if a driver's head position changes when becoming tired or falling asleep. Another proposed approach is to monitor deviation from lane markings on the road, alerting the driver when such deviations rise to dangerous levels. This approach requires a monitor built into the vehicle. Such a system is very costly, however, and not necessarily effective based upon differing driver preferences.

A driver alert system that can detect driver fatigue or sleepiness in a cost effective manner, while also avoiding the natural differences that are present in different drivers would be useful.

SUMMARY

An exemplary vehicle operator alertness monitoring system includes a heart rate monitor and a vehicle operator alert module. The vehicle operator alert module communicates with the heart rate monitor and determines whether a vehicle operator's heart rate is within an acceptable range that is based on a baseline heart rate specific to the vehicle operator. The vehicle operator alert module is configured to alert the vehicle operator when the vehicle operator's heart rate is outside of the acceptable range to assist the vehicle operator in maintaining alert control over the vehicle.

An exemplary method for assisting a vehicle operator to maintain alert control over a vehicle includes determining whether a vehicle operator's heart rate is within an acceptable range that is based on a baseline heart rate specific to the vehicle operator. The vehicle operator is alerted when the heart rate deviates from the acceptable range.

The various features and advantages of this disclosure will become apparent to those skilled in the art from the following detailed description. The drawings that accompany the detailed description can be briefly described as follows.

DETAILED DESCRIPTION

Figure 1:
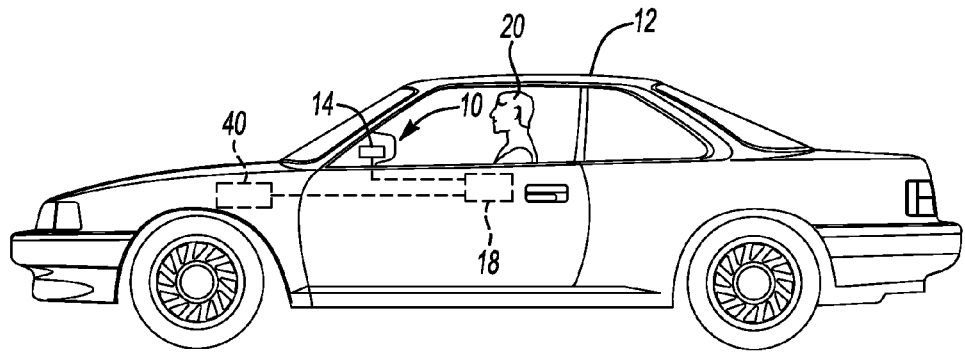
FIG. 1 schematically shows an example vehicle operator alertness monitoring system.

FIG. 1 schematically shows selected portions of an example vehicle operator alertness monitoring system 10. In this example, the system 10 is in use within a vehicle 12. The drawing shows a passenger car as one example type of vehicle. The system 10 may also be used with other types of automobiles and other vehicles such as planes and boats. For discussion purposes, an automobile and driver will be considered and those skilled in the art will realize how the following discussion may apply to pilots of planes or boats. The disclosed system is not necessarily limited to a specific type of vehicle.

The example system 10 includes a vehicle operator alert module 14 and a heart rate monitor 18. The vehicle operator alert module 14 may be supported on the dashboard or be part of the instrument panel, for example. The heart rate monitor 18 may be a device that is worn by a driver 20 or supported in the interior of the vehicle 12 in a manner that allows the heart rate monitor 18 to gather information regarding the driver's 20 heart rate.

In one example, the heart rate monitor 18 comprises a commercially available device. There are a variety of heart rate monitors 18 that are available and those skilled in the art who have the benefit of this description will realize what configuration will suit their particular needs. The heart rate monitor 18 provides information regarding a driver's heart rate to the vehicle operator alert module 14 so that the driver 20 can be alerted when the heart rate information indicates that the driver 20 may be falling asleep, for example.

In one example, the heart rate monitor 18 is wirelessly connected to the vehicle operator alert module 14. In another example, a hardwired or physical link, such as a USB connection, connects the vehicle operator alert module 14 and heart rate monitor 18.

Figure 2:
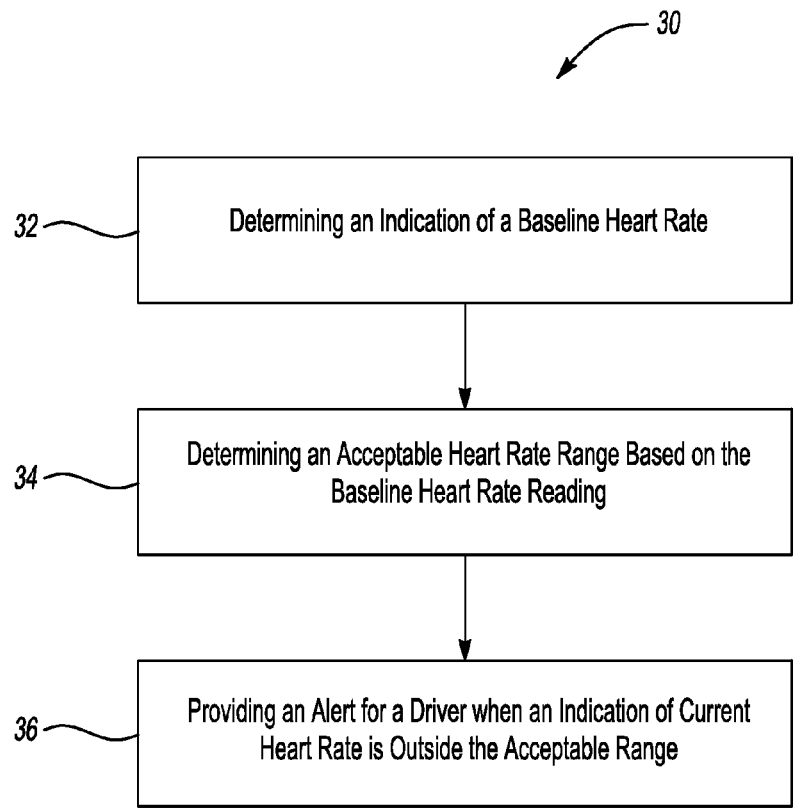
FIG. 2 shows an example method.

FIG. 2 includes a flow chart 30 that summarizes an example method of using the system 10. The system 10 can be initiated manually by the driver 20 or automatically in response to an event, such as turning on the vehicle ignition. As shown at 32, the vehicle operator alert module 14 begins by determining an initial heart rate. The heart rate monitor 18 provides an indication of the driver's current heart rate to the vehicle operator alert module 14. The indication may be a numerical indication of a number of beats per minute, a signal amplitude, or a signal frequency. The indication corresponds to a number of beats per minute or some other measurable parameter that is indicative of the driver's 20 heart rate as detected by the heart rate monitor 18. The vehicle operator alert module 14 includes a processor and sufficient programming to determine the heart rate from the indication provided by the heart rate monitor 18.

The determined initial heart rate also provides a baseline heart rate indication. Determining a baseline or normal heart rate that is specific to each driver provides the ability to account for variations in baseline heart rates for different drivers or the same driver under different conditions. In one example, the baseline reading can be retaken at the driver's request during system operation.

The vehicle operator alert module 14 is programmed to determine an acceptable heart rate range based on the baseline heart rate indication. In FIG. 2, this is shown at 34. In one example, the vehicle operator alert module 14 automatically determines and sets the acceptable heart rate range.

In another example, the vehicle operator alert module 14 automatically adds a predetermined increment above and below the determined baseline heart rate to accommodate acceptable variations in heart rate. For example, if the baseline heart rate is 65 beats per minute, the vehicle operator alert module 14 may automatically set the acceptable range at 60 to 70 beats per minute (i.e., adding and subtracting a five beat increment).

In another example, the driver 20 has the option of manually setting the acceptable range 54 or adjusting an automatically set range. For example, the driver 20 has the option of manually providing an indication of a desired maximum percentage change in heart rate or a desired maximum number of beats per minute variation from the baseline heart rate. In one example, the driver 20 has the option to input the exact values indicating a maximum acceptable heart rate and an acceptable minimum heart rate.

Manual range settings can be useful for situations in which the driver 20 believes that the baseline heart rate may not provide the most reliable basis for automatically setting the acceptable range. For example, when the driver 20 knows that she is already tired when initiating the acceptable range, manual input would be useful for making the difference between the minimum acceptable heart rate and the baseline rate less than it might be if the range were set entirely automatically. Similarly, if the driver 20 recently drank coffee, it may be useful to adjust the range to be based on a heart rate that is lower than the baseline indication obtained by the heart rate monitor 18.

One example allows the driver 20 to customize other features such as a time during which the current acceptable range will be in effect. For example, a driver 20 may expect that the effects of caffeine will dissipate after twenty or thirty minutes and want the range to be reset based upon the driver's 20 heart rate at that time. The driver in one such example sets a timer that causes the vehicle operator alert module 14 to recalibrate the acceptable range at the specified time or upon detecting a lower average heart rate reading over a selected amount of time.

The vehicle operator alert module 14 periodically (e.g., at a preset interval) or continuously receives an indication of the driver's current heart rate while the driver 20 is driving. The vehicle operator alert module 14 determines if the current heart rate is outside the acceptable range and provides an alert to the driver at 56 when the heart rate is outside the acceptable range. The alert may be audible (e.g., a beep or alarm), tactile (e.g., vibration) or visual (e.g., a blinking light) or a combination of two or more of these. The alert is intended to awaken the driver 20 who may have fallen asleep or to at least provide an indication to the driver 20 that his awareness may be reduced because he is tired. The driver 20 can then decide whether he is too tired to continue driving given his current condition.

If the driver's heart rate exceeds the acceptable range, that may indicate an excited state of mind, such as would occur when driving at excessive speeds. A warning from the vehicle operator alert module 14 would serve as a reminder to the driver 20 that he may be driving unsafely. Alternatively, crossing the upper bound of the acceptable range due to increased heart rate may indicate a cardiac event such as a heart attack or that an accident has occurred. In one example, the vehicle operator alert module 14 is configured to communicate with another device 40 supported on the vehicle 12 that is configured to communicate information to an outside service that may facilitate sending assistance to the location of the vehicle 12.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

I claim:

1. A vehicle operator alertness monitoring system comprising:
    a heart rate monitor that provides an indication of a vehicle operator's heart rate; and
    a vehicle operator alert module in communication with the heart rate monitor, the vehicle operator alert module being configured to determine an acceptable heart rate range based on a baseline heart rate that is specific to the vehicle operator and to provide an alert responsive to the indication of the vehicle operator's heart rate indicating a heart rate that is outside the acceptable range, the alert assisting the vehicle operator to remain alert, wherein the acceptable range is applicable for a first time period and a second acceptable range is determined based upon the vehicle operator's heart rate at the end of the first time period.

2. The system of claim 1, wherein the heart rate monitor is in wireless communication with the vehicle operator alert module.

3. The system of claim 1, wherein the vehicle operator alert module is configured to determine the acceptable heart rate range based at least partially on an input from the vehicle operator.

4. The system of claim 3, wherein the input is at least one of a maximum acceptable heart rate or a minimum acceptable heart rate.

5. The system of claim 3, wherein the input comprises manually entered information selected by the vehicle operator.

6. The system of claim 1, wherein the heart rate monitor provides an indication of the vehicle operator's heart rate at a set time interval.

7. A method of assisting a vehicle operator to remain alert while operating a vehicle, comprising the steps of:
    determining an indication of a baseline heart rate that is specific to the vehicle operator;
    determining an acceptable range for a heart rate based on the baseline heart rate;
    providing an alert for the vehicle operator when an indication of a current heart rate of the vehicle operator indicates that the current heart rate is outside the acceptable range;
    determining a time period for using the acceptable range; and
    determining a second acceptable range at the end of the time period.

8. The method of claim 7, wherein the alert is one of an audible alert, a visual alert, or a tactile alert.

9. The method of claim 7, wherein determining the acceptable range for the heart rate based on the baseline heart rate comprises adding a predetermined increment above and below the baseline heart rate.

10. The method of claim 7, further including updating the baseline heart rate in response to a request of the vehicle operator.

11. The method of claim 7, further including communicating information to a third party responsive to providing the alert.

12. The method of claim 7, wherein the indication is one of an indication of a number of beats per minute, a signal frequency corresponding to the current heart rate, and a signal amplitude corresponding to the current heart rate.

13. The method of claim 7, further including receiving an input from the vehicle operator for at least partially determining the acceptable range for the heart rate.

14. The method of claim 13, wherein the input includes an indication of at least a selected allowable maximum percentage change in heart rate.

15. The method of claim 13, wherein the input includes a maximum acceptable heart rate and a minimum acceptable heart rate.

16. The method of claim 13, wherein determining the indication of the baseline heart rate is initiated in response to turning on a vehicle ignition.

17. The method of claim 13, wherein the input includes an indication of at least a selected allowable maximum number of beats per minute variation from the baseline heart rate.

18. The method of claim 13, wherein the input comprises manually entered information selected by the vehicle operator.

* * * * *